United States Patent [19]
Brenner

[11] Patent Number: 5,807,981
[45] Date of Patent: Sep. 15, 1998

[54] PEPTIDES WHICH ARE CLEAVED BY C-PROTEINASE

[75] Inventor: Mitch Brenner, Moutain View, Calif.

[73] Assignee: FibroGen Inc., South San Francisco, Calif.

[21] Appl. No.: 572,225

[22] Filed: Dec. 13, 1995

[51] Int. Cl.$^6$ .......................... A61K 38/04; A61K 38/00; C07K 1/00

[52] U.S. Cl. .......................... 530/327; 530/328; 530/345; 530/409; 530/410

[58] Field of Search .................................. 530/328, 329, 530/345, 409, 410, 327

[56] References Cited

U.S. PATENT DOCUMENTS

| | | | |
|---|---|---|---|
| 4,640,893 | 2/1987 | Mangel et al. | 435/23 |
| 4,877,864 | 10/1989 | Wang et al. | 514/12 |
| 5,108,922 | 4/1992 | Wang et al. | 435/365.1 |

FOREIGN PATENT DOCUMENTS

| | | | |
|---|---|---|---|
| PCT/US87/01537 | 1/1988 | WIPO . | |

OTHER PUBLICATIONS

Bitter et al., 1987, "[33] Expression and Secretion Vectors for Yeast", *Methods in Enzymol.* 153:516–544.
Bond and Beynon, 1995, "The astacin family of metalloendopeptidases", *Protein Science* 4:1247–1261.
Bornstein and Traub, 1979, in: *The Proteins* (eds. Neurath, H. and Hill, R.H.), Academic Press, New York, pp. 412–632.
Brisson et al., 1984, "Expressions of a bacterial gene in plants by using a viral vector", *Nature* 310:511–514.
Broglie et al., 1984, "Light–Regulated Expression of a Pea Ribulose–1,5–Bisphosphate Carboxylase Small Subunit Gene in Transformed Plant Cells", *Science* 224:838–843.
Caruthers et al., 1980, "New chemical methods for sythesizing polynucleotides", *Nucleic Acids Res. Symp. Ser.* 7:215–233.
Chow et al., 1981, "Synthesis of oligodeoxyribonucleotides on silica gel support", *Nucleic Acids Res.* 9:2807–2817.
Colberre–Garapin et al., 1981, "A New Dominant Hybrid Selective Marker for Higher Eukaryotic Cells", *J. Mol. Biol.* 150:1.
Coruzzi et al., 1984, "Tissue–specific and light–regulated expression of a pea nuclear gene encoding the small subunit of ribulose–1,5–bisphosphate Carboxylase", *EMBO J.* 3:1671–1680.
Crea and Horn, 1980, "Synthesis of oligonucleotides on cellulose by a phosphotriester method", *Nucleic Acids Res.* 9:2331.
Davidson et al., 1979, "Procollagen Processing: Limited Proteolysis of COOH–Terminal Extension Peptides by a Cathepsin–Like Protease Secreted by Tendon Fibroblasts", *Eur. J. Biochem.* 100:551.
Duskin et al., 1978, "The Role of Glycosylation in the Enzymatic Conversion of Procollagen to Collagen: Studies Using Tunicamycin and Concanavalin A", *Arch. Biochem. Biophys.* 185:326–332.

Fessler and Fessler, 1978, "Biosynthesis of Procollagen", *Annu. Rev. Biochem.* 47:129–162.
Fukagawa et al, 1994, "Embryonic Expression of Mouse Bone Morphogenetic Protein–1 (BMP–1), Which is Related to the Drosophila Dorsoventral Gene *tolloid* and Encodes a Putative Astacin Metalloendopeptidase", *Developmental Biology* 163:175–183.
Goldberg et al., 1975, "Procollagen Peptidase: Its Mode of Action on the Native Substrate", *Cell* 4:45–50.
Gurley et al., 1986, "Upstream Sequences Required for Efficient Expression of a Soybean Heat Shock Gene",*Mol. Cell. Biol.* 6:559–565.
Hartman and Mulligan, 1988, "Two dominant–acting selectable markers for gene transfer studies in mammalian cells", *Proc. Natl. Acad. Sci. USA* 85:8047.
Hojima et al., 1985, "Type I Procollagen Carboxyl–terminal Proteinase from Chick Embryo Tendons—Purication and Characterization", *J. Biol. Chem.* 260:15996–16003.
Inouye and Inouye, 1985, "Up–promoter mutations in the Ipp gene of *Escherichia coli* ", *Nucleic Acids Res.* 13:3101–3109.
Kessler and Goldberg, 1978, "A Method for Assaying the Activity of the Endopeptidase Which Excises the Nonhelical Carbozyterminal Extensions from Type I Procollagen", *Anal. Biochem.* 86:463–469.
Kessler and Adar, 1989, "Type I procollagen C–proteinase from mouse fibroblasts: Purification and demonstration of a 55–k Da enhancer glycoprotein", *Eur. J. Biochem.* 186:115–121.
Kessler et al., 1986, "Partial Purification and Characterization of a Procollagen C–Proteinase from the culture Medium of Mouse Fibroblasts", *Collagen Relat. Res.* 6:249–266.
Kivirikko et al., 1984, in: *Extracellular Matrix Biochemistry* (eds. Piez, K.A. and Reddi, A.H.), Elsevier Science Publishing Co., Inc., New York, pp. 83–118.

(List continued on next page.)

*Primary Examiner*—Eric Grimes
*Assistant Examiner*—Elizabeth Slobodyansky
*Attorney, Agent, or Firm*—Pennie & Edmonds LLP

[57] ABSTRACT

The present invention is directed to the isolation and identification of the nucleic acid sequence encoding C-proteinase, the recognition of such protein's activity and applications, and tools, processes, and methods of use thereof. The invention is further directed to the identification of molecules modulating C-proteinase's activity, and methods, processes and tools therefor. In a more specific aspect, the invention is directed to peptides resembling the C-proteinase recognition site of procollagen. Such peptides may be employed as modulators of C-proteinase activity, by, for example, acting as competitive inhibitor, and may be employed for the treatment of disorders which involve unregulated production of collagen. Furthermore, such peptides may be employed as C-proteinase substrates for screening of molecules to identify compounds which modulate C-proteinase's activity.

14 Claims, No Drawings

OTHER PUBLICATIONS

Kuhn, 1987, in: *Structure and Function of Collagen Types* (eds. Mayne, R. and Burgeson, R.E.), Academic Press, Inc., Orlando, Fl., pp. 1–42.

Leung et al., 1979, "Separate Amino and Carboyxl Procollagen Peptidases in Chick Embryo Tendon", *J. Biol. Chem.* 254:224–232.

Logan and Shenk, 1984, "Adenovirus tripartite leader sequence enhances translation of mRNAs late after infection", *Proc. Natl. Acad. Sci. USA* 81:3655–3659.

Lowy et al., 1980, "Isolation of Transforming DNA: Cloning the Hamster aprt Gene", *Cell* 22:817.

Mackett et al., 1984, "General Method for Production and Selection of Infectious Vaccinia Virus Recombinants Expressing Foreign Genes", *J. Virol.* 49:857–864.

Mackett et al., 1982, "Vaccinia virus: A selectable eukaryotic cloning and expression vector", *Proc. Natl. Acad. Sci. USA* 79;7415–7419.

Matteucci and Caruthers, 1980, "The Synthesis Of Oligodeoxypyrimidines On A Polymer Support", *Tetrahedron Letters* 21:719.

Miyazono et al, 1988, "Latent High Molecular Weight Complex of Tranforming Growth Factor β1 Purification from Human Platelets and Structural Characterization", *J. Biol. Chem.* 263:6407.

Mulligan and Berg, 1981, "Selection for animal cells that expresses the *Escherichia coli* gene coding for xanthine–guanine phosphoribosyltransferase", *Proc. Natl. Acad. Sci. USA* 78:2072.

Ngyen et al., 1994, "Characterization of *tolloid–related*–1: A BMP–1–like Product That Is Required during Larval and Pupal Stages of Drosophila Development", *Developmental Biology* 166: 569–586.

Njieha et al., 1982, "Partial Purification of a Procollagen C–Proteinase. Inhibition by Synthetic Peptides and Sequential Cleavage of Type I Procollagen", *Biochemistry* 21:757–764.

O'Hare et al., 1981, "Transformation of mouse fibroblasts to methotrexate resistance by a recombinant plasmid expressing a prokaryotic dihydrofolate reductase", *Proc. Natl. Acad. Sci. USA* 78:1527.

Panicali and Paoletti, 1982, "Construction of poxviruses of cloning vectors: Insertion of the *thymidine kinase* gene from herpe simplex virus into the DNA of infections vaccinia virus", *Proc. Natl. Sci. USA* 79:4927–4931.

Prockop and Kivirikko, 1984, "Heritable Diseases of Collagen", *N. Engl. J. Med.* 311:376–383.

Ruther and Müller–Hill, 1983, "Easy identification of cDNA clones", *EMBO J.* 2:1791.

Ryhänen et al., 1982, "Conversion of Type II Procollagen to Collagen in Vitro: Removal of the Carboxy–Terminal Extension Is Inhibited by Several Naturally Occuring Amino Acids, Polyamines, and Structurally Related Compounds", *Arch. Biochem. Biophys.* 215:230–236.

Santerre et al., 1984, "Expression of prokaryotic genes for hygromycin B and G418 resistance as dominant–selection markers in mouse L cells", *Gene* 30:147–156.

Smith et al., 1983, "Molecular Engineering of the *Autographa californica* Nuclear Polyhedrosis Virus Genome: Deletion Mutations Within the Polyhedrin Gene", *J. Viol.* 46:584–593.

Szybalska and Szybalski, 1962, "Genetics of Human Cell Lines, IV. DNA–Mediated Heritable Transformation of a Biochemical Trait", *Proc. Natl. Acad. Sci. USA* 48:2026–2034.

Takahara et al., 1994, "Type I Procollagen COOH–terminal Proteinase Enhancer Protein: Identification, Primary Structure, and Chromosomal Locatization of the Cognate Human Gene (PCOLCE)", *J. Biol. Chem.* 269:26280–26285.

Takamatsu et al., 1987, "Expression of bacterial *Chloramphenicol acetyltransferase* gene in tobacco mediated by TMV–RNA", *EMBO J.* 6:307–311.

Titany et al., 1987, "Amino Acid Sequence of a Unique Protease from the Crayfish *Astacus fluviatillis*", *Biochemistry* 26:222–226.

Van Heeke and Schuster, 1989, "Expression of Human Asparagine Synthetase in *Escherichia coli*", *J. Biol. Chem.* 264:5503–5509.

Wigler et al., 1977, "Transfer of Purified Herpes Virus Thymidine Kinase Gene to Cultured Mouse Cells", *Cell* 11:223–232.

Wigler et al., 1980, "Transformation of mammalian cells with an amplifiable dominant–acting gene", *Proc. Natl. Acad. Sci. USA* 77:3567.

Wozney et al., 1988, "Noval Regulators of Bone Formation: Molecular Clones and Activities", *Science* 242:1528–1534.

Yaron et al., 1979, "Intramolecularly Quenched Fluorogenic Substrates for Hydrolytic Enzymes", *Analytical Biochemistry* 95:228–235.

Ala–Kokko et al., (1989) *Biochem. J.* 260, 509–516.

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 788 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:1:

```
Met  Pro  Gly  Val  Ala  Arg  Leu  Pro  Leu  Leu  Leu  Gly  Leu  Leu  Leu  Leu
1              5                             10                         15

Pro  Arg  Pro  Gly  Arg  Pro  Leu  Asp  Leu  Ala  Asp  Tyr  Thr  Tyr  Asp  Leu
              20                      25                     30

Ala  Glu  Glu  Asp  Asp  Ser  Glu  Pro  Leu  Asn  Tyr  Lys  Asp  Pro  Cys  Lys
         35                      40                     45

Ala  Ala  Ala  Phe  Leu  Gly  Asp  Ile  Ala  Leu  Asp  Glu  Glu  Asp  Leu  Arg
         50                      55                     60
```

-continued

| | | | | | | | | | | | | | | | |
|---|---|---|---|---|---|---|---|---|---|---|---|---|---|---|---|
| Ala 65 | Phe | Gln | Val | Gln 70 | Gln | Ala | Val | Asp | Leu 75 | Arg | Arg | His | Thr | Ala | Arg 80 |
| Lys | Ser | Ser | Ile | Lys 85 | Ala | Ala | Val | Pro | Gly 90 | Asn | Thr | Ser | Thr | Pro 95 | Ser |
| Cys | Gln | Ser | Thr 100 | Asn | Gly | Gln | Pro | Gln 105 | Arg | Gly | Ala | Cys | Gly 110 | Arg | Trp |
| Arg | Gly | Arg 115 | Ser | Arg | Ser | Arg | Arg 120 | Cys | Pro | Ala | Cys | Gly 125 | Glu | Thr | Leu |
| Gln | Asp 130 | Ser | Thr | Gly | Asn | Phe 135 | Ser | Ser | Pro | Glu | Tyr 140 | Pro | Asn | Gly | Tyr |
| Ser 145 | Ala | His | Met | His | Cys 150 | Val | Trp | Arg | Ile | Ser 155 | Val | Thr | Pro | Gly | Glu 160 |
| Lys | Ile | Ile | Leu | Asn 165 | Phe | Thr | Ser | Leu | Asp 170 | Leu | Tyr | Arg | Ser | Arg 175 | Leu |
| Cys | Trp | Tyr | Asp 180 | Tyr | Val | Glu | Val | Arg 185 | Asp | Gly | Phe | Trp | Arg 190 | Lys | Ala |
| Pro | Leu | Arg 195 | Gly | Arg | Phe | Cys | Gly 200 | Ser | Lys | Leu | Pro | Glu 205 | Pro | Ile | Val |
| Ser | Thr 210 | Asp | Ser | Arg | Leu | Trp 215 | Val | Glu | Phe | Arg | Ser 220 | Ser | Ser | Asn | Trp |
| Val 225 | Gly | Lys | Gly | Phe | Phe 230 | Ala | Val | Tyr | Glu | Ala 235 | Ile | Cys | Gly | Gly | Asp 240 |
| Val | Lys | Lys | Asp | Tyr 245 | Gly | His | Ile | Gln | Ser 250 | Pro | Asn | Tyr | Pro | Asp 255 | Asp |
| Tyr | Arg | Pro | Ser 260 | Lys | Val | Cys | Ile | Trp 265 | Arg | Ile | Gln | Val | Ser 270 | Glu | Gly |
| Phe | His | Val 275 | Gly | Leu | Thr | Phe | Gln 280 | Ser | Phe | Glu | Ile | Glu 285 | Arg | His | Asp |
| Ser | Cys 290 | Ala | Tyr | Asp | Tyr | Leu 295 | Glu | Val | Arg | Asp | Gly 300 | His | Ser | Glu | Ser |
| Ser 305 | Thr | Leu | Ile | Gly | Arg 310 | Tyr | Cys | Gly | Tyr | Glu 315 | Lys | Pro | Asp | Asp | Ile 320 |
| Lys | Ser | Thr | Ser | Ser 325 | Arg | Leu | Trp | Leu | Lys 330 | Phe | Val | Ser | Asp | Gly 335 | Ser |
| Ile | Asn | Lys | Ala 340 | Gly | Phe | Ala | Val | Asn 345 | Phe | Phe | Lys | Glu | Val 350 | Asp | Glu |
| Cys | Ser | Arg 355 | Pro | Asn | Arg | Gly | Gly 360 | Cys | Glu | Gln | Arg | Cys 365 | Leu | Asn | Thr |
| Leu | Gly 370 | Ser | Tyr | Lys | Cys | Ser 375 | Cys | Asp | Pro | Gly | Tyr 380 | Glu | Leu | Ala | Pro |
| Asp 385 | Lys | Arg | Arg | Cys | Glu 390 | Ala | Ala | Cys | Gly | Gly 395 | Phe | Leu | Thr | Lys | Leu 400 |
| Asn | Gly | Ser | Ile | Thr 405 | Ser | Pro | Gly | Trp | Pro 410 | Lys | Glu | Tyr | Pro | Pro 415 | Asn |
| Lys | Asn | Cys | Ile 420 | Trp | Gln | Leu | Val | Ala 425 | Pro | Thr | Gln | Tyr | Arg 430 | Ile | Ser |
| Leu | Gln | Phe 435 | Asp | Phe | Phe | Glu | Thr 440 | Glu | Gly | Asn | Asp | Val 445 | Cys | Lys | Tyr |
| Asp | Phe 450 | Val | Glu | Val | Arg | Ser 455 | Gly | Leu | Thr | Ala | Asp 460 | Ser | Lys | Leu | His |
| Gly 465 | Lys | Phe | Cys | Gly | Ser 470 | Glu | Lys | Pro | Glu | Val 475 | Ile | Thr | Ser | Gln | Tyr 480 |
| Asn | Asn | Met | Arg | Val 485 | Glu | Phe | Lys | Ser | Asp 490 | Asn | Thr | Val | Ser | Lys 495 | Lys |

| | | | | | | | | | | | | | | |
|---|---|---|---|---|---|---|---|---|---|---|---|---|---|---|
| Gly | Phe | Lys | Ala<br>500 | His | Phe | Phe | Ser | Asp<br>505 | Lys | Asp | Glu | Cys<br>510 | Ser | Lys | Asp |
| Asn | Gly | Gly<br>515 | Cys | Gln | Gln | Asp | Cys<br>520 | Val | Asn | Thr | Phe<br>525 | Gly | Ser | Tyr | Glu |
| Cys | Gln<br>530 | Cys | Arg | Ser | Gly | Phe<br>535 | Val | Leu | His | Asp<br>540 | Asn | Lys | His | Asp | Cys |
| Lys<br>545 | Glu | Ala | Gly | Cys | Asp<br>550 | His | Lys | Val | Thr | Ser<br>555 | Thr | Ser | Gly | Thr | Ile<br>560 |
| Thr | Ser | Pro | Asn | Trp<br>565 | Pro | Asp | Lys | Tyr | Pro<br>570 | Ser | Lys | Lys | Glu | Cys<br>575 | Thr |
| Trp | Ala | Ile | Ser<br>580 | Ser | Thr | Arg | Gly | His<br>585 | Arg | Val | Lys | Leu | Thr<br>590 | Phe | Met |
| Glu | Met | Asp<br>595 | Ile | Glu | Ser | Gln | Pro<br>600 | Glu | Cys | Ala | Tyr | Asp<br>605 | Thr | Leu | Glu |
| Val | Phe | Asp<br>610 | Gly | Arg | Asp | Arg | Lys<br>615 | Ala | Pro | Val | Leu | Gly<br>620 | Arg | Phe | Cys |
| Gly<br>625 | Ser | Lys | Lys | Pro | Glu<br>630 | Pro | Val | Leu | Ala | Thr<br>635 | Gly | Ser | Arg | Met | Phe<br>640 |
| Leu | Arg | Phe | Tyr | Ser<br>645 | Lys | Asn | Ser | Val | Gln<br>650 | Arg | Lys | Gly | Phe | Gln<br>655 | Ala |
| Ser | His | Ala | Glu<br>660 | Cys | Gly | Gly | Gln | Val<br>665 | Arg | Ala | Asp | Val | Lys<br>670 | Thr | Lys |
| Asp | Leu | Thr<br>675 | Tyr | Ser | Gln | Pro | Gln<br>680 | Phe | Gly | Asp | Asn | Asn<br>685 | Tyr | Pro | Gly |
| Gly | Val<br>690 | Asp | Cys | Glu | Trp | Val<br>695 | Ile | Val | Ala | Glu | Glu<br>700 | Gly | Tyr | Gly | Val |
| Glu<br>705 | Leu | Val | Phe | Gln | Thr<br>710 | Phe | Glu | Val | Glu | Glu<br>715 | Glu | Thr | Asp | Cys | Gly<br>720 |
| Tyr | Asp | Tyr | Met | Glu<br>725 | Leu | Phe | Asp | Gly | Tyr<br>730 | Asp | Ser | Thr | Ala | Pro<br>735 | Arg |
| Leu | Gly | Arg | Tyr<br>740 | Cys | Arg | Ser | Gly | Leu<br>745 | Pro | Glu | Glu | Val | Tyr<br>750 | Ser | Ala |
| Gly | Asp | Ser<br>755 | Val | Lys | Val | Lys | Phe<br>760 | His | Ser | Asp | Asp | Thr<br>765 | Ile | Thr | Lys |
| Lys | Gly<br>770 | Phe | His | Leu | Arg | Tyr<br>775 | Thr | Ser | Thr | Lys | Phe<br>780 | Gln | Asp | Thr | Leu |
| His | Ser | Arg | Lys<br>785 | | | | | | | | | | | | |

( 2 ) INFORMATION FOR SEQ ID NO:2:

( i ) SEQUENCE CHARACTERISTICS:
        ( A ) LENGTH: 198 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Ala<br>1 | Ala | Thr | Ser | Arg<br>5 | Pro | Glu | Arg | Val | Trp<br>10 | Pro | Asp | Gly | Val | Ile<br>15 | Pro |
| Phe | Val | Ile | Gly<br>20 | Gly | Asn | Phe | Thr | Gly<br>25 | Ser | Gln | Arg | Ala | Val<br>30 | Phe | Arg |
| Gln | Ala | Met<br>35 | Arg | His | Trp | Glu | Lys<br>40 | His | Thr | Cys | Val | Thr<br>45 | Phe | Leu | Glu |

```
Arg Thr Asp Glu Asp Ser Tyr Ile Val Phe Thr Tyr Arg Pro Cys Gly
     50              55                 60

Cys Cys Ser Tyr Val Gly Arg Arg Gly Gly Gly Pro Gln Ala Ile Ser
65              70              75                          80

Ile Gly Lys Asn Cys Asp Lys Phe Gly Ile Val Val His Glu Leu Gly
                85              90                      95

His Val Val Gly Phe Trp His Glu His Thr Arg Pro Asp Arg Asp Arg
            100             105                 110

His Val Ser Ile Val Arg Glu Asn Ile Gln Pro Gly Gln Glu Tyr Asn
        115             120                 125

Phe Leu Lys Met Glu Pro Gln Glu Val Glu Ser Leu Gly Glu Thr Tyr
    130             135                 140

Asp Phe Asp Ser Ile Met His Tyr Ala Arg Asn Thr Phe Ser Arg Gly
145             150                 155                     160

Ile Phe Leu Asp Thr Ile Val Pro Lys Tyr Glu Val Asn Gly Val Lys
            165             170                     175

Pro Pro Ile Gly Gln Arg Thr Arg Leu Ser Lys Gly Asp Ile Ala Gln
            180             185                 190

Ala Arg Lys Leu Tyr Lys
            195
```

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1..8
        (D) OTHER INFORMATION: /note= "Acetylated at
            amino- terminus and amidated at carboxy-terminus"

(xi) SEQUENCE DESCRIPTION: SEQ ID NO:3:

```
Tyr Tyr Arg Ala Asp Asp Ala Asn
1               5
```

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1..8
        (D) OTHER INFORMATION: /note= "Acetylated at the
            amino- terminus and amidated at the carboxy-terminus"

(xi) SEQUENCE DESCRIPTION: SEQ ID NO:4:

```
Phe Tyr Arg Ala Asp Gln Pro Arg
1               5
```

(2) INFORMATION FOR SEQ ID NO:5:

(i) SEQUENCE CHARACTERISTICS:
        (A) LENGTH: 8 amino acids
        (B) TYPE: amino acid ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1..8
        ( D ) OTHER INFORMATION: /note= "Acetylated at the
            amino- terminus and amidated at the carboxy-terminus"

( x i ) SEQUENCE DESCRIPTION: SEQ ID NO:5:

Tyr  Met  Arg  Ala  Asp  Gln  Ala  Ala
    1                   5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1..8
        ( D ) OTHER INFORMATION: /note= "Acetylated at the
            amino- terminus and amidated at the carbosy-terminus"

( x i ) SEQUENCE DESCRIPTION: SEQ ID NO:6:

Pro  Tyr  Tyr  Gly  Asp  Glu  Pro  Met
    1                   5

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1..12
        ( D ) OTHER INFORMATION: /note= "Acetylated at the
            amino- terminus and amidated at the carboxy-terminus"

( x i ) SEQUENCE DESCRIPTION: SEQ ID NO:7:

Phe  Ala  Pro  Tyr  Tyr  Gly  Asp  Glu  Pro  Met  Asp  Phe
    1                   5                   1 0

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1..7
        ( D ) OTHER INFORMATION: /note= "Acetylated at
            amino- terminus and amidated at the carboxy-terminus"

( x i ) SEQUENCE DESCRIPTION: SEQ ID NO:8:

Pro  Tyr  Tyr  Gly  Asp  Glu  Pro

```
            1               5
```

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1..6
        (D) OTHER INFORMATION: /note= "Acetylated at the
            amino- terminus and amidated at the carboxy-terminus"

(xi) SEQUENCE DESCRIPTION: SEQ ID NO:9:

```
Pro  Tyr  Tyr  Gly  Asp  Glu
1                    5
```

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1..5
        (D) OTHER INFORMATION: /note= "Acetylated at the
            amino- terminus and amidated at the carboxy-terminus"

(xi) SEQUENCE DESCRIPTION: SEQ ID NO:10:

```
Pro  Tyr  Tyr  Gly  Asp
1                    5
```

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Modified-site
        (B) LOCATION: 1..7
        (D) OTHER INFORMATION: /note= "Acetylated at
            amino- terminus and amidated at carboxy-terminus"

(xi) SEQUENCE DESCRIPTION: SEQ ID NO:11:

```
Tyr  Tyr  Gly  Asp  Glu  Pro  Met
1                    5
```

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (ix) FEATURE:

(A) NAME/KEY: Modified-site
            (B) LOCATION: 1..6
            (D) OTHER INFORMATION: /note= "Acetylated at
                amino- terminus and amidated at carboxy-terminus"

(xi) SEQUENCE DESCRIPTION: SEQ ID NO:12:

Tyr  Gly  Asp  Glu  Pro  Met
   1                    5

(2) INFORMATION FOR SEQ ID NO:13:

(i) SEQUENCE CHARACTERISTICS:
            (A) LENGTH: 5 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Modified-site
            (B) LOCATION: 1..5
            (D) OTHER INFORMATION: /note= "Acetylated at
                amino- terminus and amidated at carboxy-terminus"

(xi) SEQUENCE DESCRIPTION: SEQ ID NO:13:

Gly  Asp  Glu  Pro  Met
   1                    5

(2) INFORMATION FOR SEQ ID NO:14:

(i) SEQUENCE CHARACTERISTICS:
            (A) LENGTH: 8 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:14:

Tyr  Tyr  Arg  Ala  Asp  Asp  Ala  Asn
   1                    5

(2) INFORMATION FOR SEQ ID NO:15:

(i) SEQUENCE CHARACTERISTICS:
            (A) LENGTH: 8 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:15:

Phe  Tyr  Arg  Ala  Asp  Gln  Pro  Arg
   1                    5

(2) INFORMATION FOR SEQ ID NO:16:

(i) SEQUENCE CHARACTERISTICS:
            (A) LENGTH: 8 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:16:

Tyr  Met  Arg  Ala  Asp  Gln  Ala  Ala
   1                    5

( 2 ) INFORMATION FOR SEQ ID NO:17:

( i ) SEQUENCE CHARACTERISTICS:
    ( A ) LENGTH: 8 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:17:

```
Pro  Tyr  Tyr  Gly  Asp  Glu  Pro  Met
1                      5
```

( 2 ) INFORMATION FOR SEQ ID NO:18:

( i ) SEQUENCE CHARACTERISTICS:
    ( A ) LENGTH: 12 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:18:

```
Phe  Ala  Pro  Tyr  Tyr  Gly  Asp  Glu  Pro  Met  Asp  Phe
1                      5                          10
```

( 2 ) INFORMATION FOR SEQ ID NO:19:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:19:

```
Pro  Tyr  Tyr  Gly  Asp  Glu  Pro
1                      5
```

( 2 ) INFORMATION FOR SEQ ID NO:20:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:20:

```
Pro  Tyr  Tyr  Gly  Asp  Glu
1                      5
```

( 2 ) INFORMATION FOR SEQ ID NO:21:

( i ) SEQUENCE CHARACTERISTICS:
    ( A ) LENGTH: 5 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:21:

```
Pro  Tyr  Tyr  Gly  Asp
1                      5
```

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:22:

```
Tyr Tyr Gly Asp Glu Pro Met
1               5
```

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:23:

```
Tyr Gly Asp Glu Pro Met
1           5
```

(2) INFORMATION FOR SEQ ID NO:24:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:24:

```
Gly Asp Glu Pro Met
1         5
```

PEPTIDES WHICH ARE CLEAVED BY C-PROTEINASE

TABLE OF CONTENTS

I. INTRODUCTION
II. BACKGROUND OF THE INVENTION
III. SUMMARY OF THE INVENTION
IV. DEFINITIONS
V. DETAILED DESCRIPTION OF THE INVENTION
  A. Isolation Of Gene Encoding C-Proteinase
  B. Uses Of The C-Proteinase Coding Sequence
  C. Expression Of C-Proteinase
  D. Identification Of Transfectants Or Transformants That Express C-Proteinase
  E. Screening Of Peptide Library With C-Proteinase Or Engineered Cell Lines
  F. Screening Of Organic Compounds With C-Proteinase Protein Or Engineered Cell Lines
  G. Generation Peptide Substrates Of C-Proteinase
VI. EXAMPLES
  A. Generation Of Peptide Substrates As C-Proteinase Inhibitors
ABSTRACT

I. INTRODUCTION

Collagen is integral to, among other things, the proper formation of connective tissue. Thus, the over- or underproduction of collagen or the production of abnormal collagen (including incorrectly processed collagen) has been linked with numerous connective tissue diseases and disorders. As a consequence of this link, control and/or modulation of collagen formation has been the focus of study, including efforts to identify the enzymes critical to collagen's proper formation and processing.

The present invention is directed to the isolation and identification of the nucleic acid sequence encoding C-proteinase, the recognition of such protein's activity and applications, and tools, processes, and methods of use thereof. The invention is further directed to the identification of molecules which are capable of modulating C-proteinase's activity, and methods, processes and tools therefor. More specifically, the invention is directed to peptides resembling the C-proteinase recognition site of procollagen. Such peptides may be employed as modulators of C-proteinase activity, by, for example, acting as a competitive inhibitor, and may be employed for the treatment of disorders which relate to the unregulated production of collagen. Furthermore, such peptides may be employed as C-proteinase substrates to screen and identify compounds which modulate C-proteinase's activity.

II. BACKGROUND OF THE INVENTION

At present nineteen types of collagens have been identified. These collagens, including fibrillar collagen types I, II, III, and VII, are synthesized as procollagen precursor molecules which contain amino- and carboxy-terminal peptide extensions. These peptide extensions, referred to as "pro-regions," are designated as N- and C-propeptides, respectively and are required for the formation of the procollagen triple helix. Other fibrillar collagen types may also be processed in this fashion.

The pro-regions are typically cleaved upon secretion of the procollagen triple helical precursor molecule from the cell to yield a mature triple helical collagen molecule. Although the cleavage site of the C-terminal propeptides have been identified (Hojima et al., 1985, *J. Biol. Chem.* 260:15996–16003), little is known about the mechanism of C-proteinase's enzymatic activity. For example, prior to the instant invention, the structural requirements of the recognition sites necessary for binding of procollagen to the active site of C-proteinase was not known. Moreover, previous attempts to cleave small peptides with C-proteinase failed. Njieha et al., 1982, *Biochemistry* 23:757–764. Upon cleavage, the "mature" collagen molecule is capable of association, for example, into highly structured collagen fibers. See e.g., Fessler and Fessler, 1978, *Annu. Rev. Biochem.* 47:129–162; Bornstein and Traub, 1979, in: *The Proteins* (eds. Neurath, H. and Hill, R. H.), Academic Press, New York, pp. 412–632; Kivirikko et al., 1984, in: *Extracellular Matrix Biochemistry* (eds. Piez, K. A. and Reddi, A. H.), Elsevier Science Publishing Co., Inc., New York, pp. 83–118; Prockop and Kivirikko, 1984, *N. Engl. J. Med.* 311:376–383; Kuhn, 1987, in: *Structure and Function of Collagen Types* (eds. Mayne, R. and Burgeson, R. E.), Academic Press, Inc., Orlando, Fla., pp. 1–42.

An array of critical diseases has been associated with unregulated production of collagen, including pathological fibrosis or scarring, such as endocardial sclerosis, idiopathic interstitial fibrosis, interstitial pulmonary fibrosis, perimuscular fibrosis, Symmers' fibrosis, pericentral fibrosis, hepatitis, dermatofibroma, billary cirrhosis, alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/ retinal separation, esophageal stricture, payronles disease. Further fibrotic disorders may be induced or initiated by surgical insults such as scar revision/plastic surgeries, glaucoma, cataract fibrosis, corneal scarring, joint adhesions, graft vs. host disease, tendon surgery, nerve entrapment, dupuytren's contracture, OB/GYN adhesions/ fibrosis, pelvic adhesions, peridural fibrosis, restenosis. One strategy for the treatment of these diseases is to inhibit the pathological overproduction or underproduction of collagen. Thus, identification and isolation of enzymes involved in collagen production and processing are of major medical interest.

C-proteinase is an enzyme that catalyzes the cleavage of the C-propeptide of, for example, fibrillar collagens, including type I, type II, and type III collagen. The enzyme was first observed in the culture media of human and mouse fibroblasts (Goldberg et al., 1975, *Cell* 4:45–50; Kessler and Goldberg, 1978, *Anal. Biochem.* 86:463–469), and chick tendon fibroblasts (Duskin et al., 1978, *Arch. Biochem. Biophys.* 185:326–332; Leung et al., 1979, *J. Biol. Chem.* 254:224–232). An acidic proteinase which removes the C-terminal propeptides from type I procollagen has also been identified. Davidson et al., 1979, *Eur. J. Biochem.* 100:551.

A partially purified protein having C-proteinase activity was obtained from chick calvaria in 1982. Njieha et al., 1982, *Biochemistry* 23:757–764. In 1985, chicken C-proteinase was isolated, purified and characterized from conditioned media of chick embryo tendons. Hojima et al., 1985, *J. Biol. Chem.* 260:15996–16003. Murine C-proteinase has been subsequently purified from media of cultured mouse fibroblasts. Kessler et al., 1986, *Collagen Relat. Res.* 6:249–266; Kessler and Adar, 1989, *Eur. J. Biochem.* 186:115–121.

Experiments conducted with these purified forms of chick and mouse C-proteinase have indicated that the enzyme is instrumental in the formation of functional collagen fibers. For example, inhibition of C-proteinase in in vitro assays has been shown to inhibit the cleavage of the C-terminal pro-regions of procollagen fibrils. Hojima et al., supra.

As a consequence of the enzyme's apparent importance to collagen production, scientists have identified a number of C-proteinase inhibitors. See e.g., Hojima et al., supra. For example, several metal chelators have demonstrated activity as a C-proteinase inhibitor. Likewise, chymostatin and pepstatin A were found to be relatively strong inhibitors of C-proteinase. Additionally, $\alpha_2$-Macroglobulin, ovostatin, and fetal bovine serum appear to at least partially inhibit C-proteinase activity.

Dithiothreitol, SDS, concanavalin A, $Zn^{2+}$, $Cu^{2+}$, and $Cd^{2+}$ were inhibitory at low concentrations and some reducing agents, several amino acids, phosphate, and ammonium sulfate were inhibitory at concentrations of 1–10 mM. Further, the enzyme was shown to be inhibited 10 by the basic amino acids lysine and arginine. Leung et al., supra; Ryhänen et al., 1982, Arch. Biochem. Biophys. 215:230–236. Also high concentrations of NaCl or Tris-HCl buffer were found to inhibit the enzyme. With 0.2, 0.3, and 0.5M NaCl, the activity was reduced 66, 38, and 25%, respectively, of that observed with the standard assay concentration of 0.15M. Tris-HCl buffer in a concentration of 0.2–0.5M markedly inhibited activity. Hojima et al., supra.

In contrast, microbial inhibitors such as leupeptin, phosphoramidon, antipain, bestatin, elastinal, and amastatin, are considered to have weak or no effect on the activity of C-proteinase.

C-proteinase activity and its inhibition have been determined using a wide array of assays. See e.g., Kessler and Goldberg, 1978, Anal. Biochem. 86:463; Njieha et al., 1982, Biochemistry 21:757–764.

Despite the availability of such assays, large scale review and testing of potential C-proteinase inhibitors has not been performed to date due to the limited availability of human C-proteinase. As articulated in numerous publications, the enzyme is difficult to isolate by conventional biochemical means and neither the enzyme nor the cDNA sequence encoding such enzyme was known to be available prior to the instant invention. Takahara et al., 1994, J. Biol. Chem. 269:26280–26285, 26284 (C-proteinase's "peptide and nucleotide sequences are as yet unavailable").

Significantly, a protein sharing the structural characteristics of C-proteinase was isolated in 1988 from bone tissue. This protein, designated BMP-1 ("bone morphogenic protein"), was identified as belonging to a TGF-$\beta$ related protein family. Wozney et al., 1988, Science 242:1528–1534. BMP-1 was isolated coincidentally with BMP-2A and BMP-3. Although evidence provides that BMP-2A and BMP-3 play a key role in the stimulation of bone development and growth, the activity of BMP-1 was never well established.

Sequence comparison reveals that BMP-1 contains a EGF-like domain and a region designated as "A-domain" having sequence similarity with a protease isolated from crayfish. Titany et al., 1987, Biochemistry 26:222. As the TGF-$\beta$1 binding protein also contains EGF-like domains, it has been suggested that BMP-1 could be a protease involved in the activation of TGF-$\beta$1. Miyazono et al., 1988, J. Biol. Chem. 263:6407; Woyznek et al., supra; Fukagawa et al., 1994, Dev. Bio. 162:175–183.

It has also been suggested that, due to homology to the Drosophila melanogaster tolloid gene product, BMP-1 is involved in the overall mechanism for the dorsal-ventral patterning of the neural tube. Ngyen et al., 1994, Developmental Biology 166:569–586; Fukagawa et al, 1994, Developmental Biology 163:175–183.

It has not been previously suggested that BMP-1 is associated with the formation of collagen. Indeed, in a most recent review article, the association of BMP-1 with the TGF-$\beta$ related proteins BMP-2 and BMP-3 has been stressed as to lead to the hypothesis that the physiological function of BMP-1 is to activate latent TGF-$\beta$. Bond and Beynon, 1995, Protein Science 4:1247–1261. Thus, while the structure of this putative bone morphogenic protein has been identified, no correct activity or use was known for this protein until the present invention, which completed the discovery of C-proteinase through the identification and proof of its utility.

III. SUMMARY OF THE INVENTION

The present invention is directed to synthesized or recombinant compositions derived from the deduced amino acid sequences and nucleic acid sequences for human C-proteinase.

In one embodiment of the present invention, the composition comprises the full-length amino acid sequence for C-proteinase. In another embodiment of the present invention, the composition comprises a C-proteinase analog, derivative or fragment thereof having C-proteinase-like activity. In yet further embodiments of the present invention, the composition is radiolabelled.

The present invention further relates to the use C-proteinase, its analogs and derivatives and fragments for use in diseases and disorders related to the abnormal production of collagen. Such polypeptides may act directly with collagen, or, alternatively, with other enzymes involved in the processing of collagen, e.g. lysyl oxidase.

The present invention also relates to the use of proteins, peptides and organic molecules capable of modulating the formation of collagen by affecting the interaction between C-proteinase and collagen precursor molecules, including procollagen, or, alternatively, other collagen processing enzymes and/or the cleavage site of C-proteinase. The invention is further directed to the use of such proteins, peptides and/or organic molecules, either alone or in combination with other molecules, in the treatment of disorders, including disorders related to abnormal collagen formation, including but not limited to rheumatoid arthritis and scleroderma.

The present invention further relates to the identification of peptides resembling the C-proteinase cleavage region of procollagen. In one specific embodiment, such peptides are cleaved by C-proteinase. Peptides resembling the C-proteinase cleavage site will compete with procollagen for the active site of C-proteinase, and therefore may serve to modulate C-proteinase activity, by, for example, acting as a competitive inhibitor. Alternately, such peptides may be used to screen molecules to identify compounds capable of modulating C-proteinase activity. In one embodiment, the peptide is attached to a fluorogenic tag. Cleavage of the peptide results in a dramatic increase of its fluorescence, and provides a convenient and powerful tool for measuring C-proteinase activity. Peptides attached to such fluorogenic tag will be particularly useful for high through-put assays for the identification of compounds capable of modulating C-proteinase activity and the formation of mature collagen.

The present invention is further related to the use of C-proteinase, whether labelled or unlabelled, as a tracer which could then be used to separate, by HPLC, the different C-proteinase derivatives to yield a carrier-free tracer, in binding assays.

IV. DEFINITIONS

"C-proteinase" shall be construed to mean an enzyme capable of processing collagen molecules, derivatives or fragments, or their precursors by cleaving through -Ala↓Asp-Asp- and/or -Gly↓Asp-Glu-. The term shall include human C-proteinase and derivatives, analogs, fragments and variants thereof having C-proteinase-like activity.

V. DETAILED DESCRIPTION OF THE INVENTION

A. Isolation of Gene Encoding C-Proteinase

The C-proteinase enzyme may be isolated to homogeneity by application of previously described procedures, including the procedures described in Hojima, et al., 1985, *J. Biol. Chem.* 260:15996. The homogenous C-proteinase enzyme may then be sequenced according to known techniques using commercially available apparatus.

Nucleic acid probes were prepared using the determined amino acid sequence for C-proteinase. Such probes may by synthetically synthesized and labelled. Preparation techniques for such probes and others are known in the art and set forth in, for example, Sambrook, et al., 1989, *Molecular Cloning, A Laboratory Manual,* 2d Edition, Cold Springs Harbor Laboratory Press, New York, at Chapters 10–11. The nucleic acid sequences obtained using such probes may be sequenced using any one of the techniques generally described in Sambrook, et al., supra, at Chapter 13.

The gene encoding C-proteinase may also be isolated by performing a polymerase chain reaction (PCR) using one or more degenerate oligonucleotide primer pools that are designed based on the deduced nucleotide sequence of C-proteinase, as deduced from the amino acid sequence of C-proteinase. The techniques used to identify the nucleic acid sequence of C-proteinase using PCR are described in, for example, Sambrook, et al., supra, at Chapter 14.

The invention also relates to unknown C-proteinase genes isolated from other species, in which C-proteinase activity exists. Members of the C-proteinase family are defined herein as those enzymes that can process procollagen molecules at the C-terminal end of such molecule. A bacteriophage cDNA library may be screened, under conditions of reduced stringency, using a radioactively labeled fragment of the human C-proteinase clone described herein. Alternatively the human C-proteinase sequence can be used to design degenerate or fully degenerate oligonucleotide probes which can be used as PCR probes or to screen bacteriophage cDNA libraries. The PCR product may be subcloned and sequenced to insure that the amplified sequences represent the C-proteinase sequences. The PCR fragment may be used to isolate a full length C-proteinase clone by radioactively labeling the amplified fragment and screening a bacteriophage cDNA library. Alternatively, the labeled fragment may be used to screen a genomic library. For a review of cloning strategies which may be used, see e.g., Sambrook, et al., 1989, *Molecular Cloning, A Laboratory Manual,* 2d Edition, Cold Springs Harbor Press, N.Y.; and Ausubel et al., 1989, Current Protocols in Molecular Biology, (Green Publishing Associates and Wiley Interscience, N.Y.)

Isolation of human C-proteinase cDNA may also be achieved by construction of a cDNA library in a mammalian expression vector such as pcDNA1, that contains SV40 origin of replication sequences which permit high copy number expression of plasmids when transferred into COS cells. The expression of C-proteinase on the surface of transfected COS cells may be detected in a number of ways known in the art. Cells expressing the human C-proteinase may be enriched by subjecting transfected cells to a FACS (fluorescent activated cell sorter) sorting.

The deduced amino acid sequence of a polynucleotide sequence encoding C-proteinase is identified as SEQ ID NO:1. The invention is further directed to polynucleotide sequences encoding peptide fragments having the functional characteristics of C-proteinase. One example of such peptide is identified as SEQ ID No:2. The invention is intended to embrace any polynucleotide encoding a peptide/polypeptide comprising fragments, analogs or functional equivalent derivatives of C-proteinase, including polynucleotides derived from any species encoding a polypeptide functionally equivalent to C-proteinase and fragments, analogs and derivatives thereof, and further including polynucleotide sequences which are genetically modified, either by natural mutation events or by recombinant techniques, being functionally equivalent to C-proteinase, and fragments, analogs and derivatives thereof. The invention is further intended to include any peptides/polypeptides derived from the described polynucleotides.

In accordance with the invention, C-proteinase nucleotide sequences which encode C-proteinase, peptide fragments of C-proteinase, C-proteinase fusion proteins or functional equivalents thereof may be used to generate recombinant DNA molecules that direct the expression of the protein or a functional equivalent thereof, in appropriate host cells. Alternatively, nucleotide sequences which hybridize to portions of the C-proteinase sequence may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the C-proteinase protein. Such DNA sequences include those which are capable of hybridizing to the human C-proteinase sequence under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the C-proteinase sequence, which result in a silent change thus producing a functionally equivalent protein. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, analine; asparagine, glutamine; serine, threonine; phenylalanine, tyrosine. As used herein, a functionally equivalent C-proteinase refers to an enzyme which can process procollagen or fragments or derivatives thereof, but not necessarily with the same binding affinity of its counterpart native C-proteinase.

The DNA sequences of the invention may be engineered in order to alter the enzyme sequence for a variety of ends including but not limited to alterations which modify processing and expression of the gene product. For example, mutations may be introduced using techniques which are well known in the art, e.g., site-directed mutagenesis to, for example, insert new restriction sites. For example, in certain expression systems such as yeast, host cells may over-glycosylate the gene product. When using such expression systems it may be preferable to alter the C-proteinase coding sequence to eliminate any N-linked glycosylation site.

In another embodiment of the invention, the C-proteinase or a modified C-proteinase sequence may be ligated to a heterologous sequence to encode a fusion protein. For example, for screening of peptide libraries it may be useful to encode a chimeric C-proteinase protein expressing a heterologous epitope that is recognized by a commercially available antibody. A fusion protein may also be engineered to contain a cleavage site located between the C-proteinase sequence and the heterologous protein sequence, so that the C-proteinase can be cleaved away from the heterologous moiety.

In an alternate embodiment of the invention, the coding sequence of C-proteinase could be synthesized in whole or in part, using chemical methods well known in the art. See, for example, Caruthers, et al., 1980, *Nucleic Acids Res. Symp. Ser.* 7:215–233; Crea and Horn, 1980, *Nucleic Acids Res.* 9(10):2331; Matteucci and Caruthers, 1980, *Tetrahedron Letters* 21:719; and Chow and Kempe, 1981, *Nucleic Acids Res.* 9(12):2807–2817. Alternatively, the protein itself could be produced using chemical methods to synthesize the C-proteinase amino acid sequence in whole or in part. For example, peptides can be synthesized by solid phase techniques, cleaved from the resin, and purified by preparative high performance liquid chromatography. (See e.g., see Creighton, 1983, *Proteins Structures And Molecular Principles,* W. H. Freeman and Co., N.Y. pp. 50–60). The composition of the synthetic peptides may be confirmed by amino acid analysis or sequencing (e.g., the Edman degradation procedure; see, Creighton, 1983, *Proteins, Structures and Molecular Principles,* W. H. Freeman and Co., N.Y., pp. 34–49).

B. Uses Of The C-Proteinase Coding Sequence

The C-proteinase coding sequence may be used for diagnostic purposes to detect C-proteinase expression. Included in the scope of the invention are oligoribonucleotide sequences, that include antisense RNA and DNA molecules and ribozymes, which function to inhibit translation of C-proteinase.

Antisense techniques are known in the art and may be applied herein.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of C-proteinase RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribo-nucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In addition, mutated forms of C-proteinase, having a dominant negative effect, may be expressed in targeted cell populations to inhibit the activity of endogenously expressed wild-type C-proteinase.

Additionally, the DNA encoding C-proteinase may also have a number of uses for the diagnosis of diseases resulting from aberrant expression of the enzyme. For example, the C-proteinase DNA sequence may be used in hybridization assays of biopsies or autopsies to diagnose abnormalities of expression (e.g., Southern or Northern blot analysis, in situ hybridization assays).

The C-proteinase cDNA may be used also as a probe to detect the expression of the C-proteinase mRNA.

In addition, the expression of C-proteinase during embryonic development may also be determined using nucleic acid encoding C-proteinase. As described in the literature, no deficiencies of C-proteinase have been found in patients with genetic diseases of connective tissues. Thus, it has been generally assumed that a genetic deficiency related to C-proteinase produces death in utero. In situ hybridizations can predict in utero problems related to connective tissue diseases.

Various modifications to the DNA molecules may be introduced as a means of increasing intracellular stability and half-life. Possible modifications include but are not limited to the addition of flanking sequences of ribo- or deoxynucleotides to the 5' and/or 3' ends of the molecule or the use of phosphorothioate or 2' O-methyl rather than phosphodiesterase linkages within the oligodeoxyribonucle-otide backbone.

C. Expression of C-Proteinase

In order to express a biologically active C-proteinase, the nucleotide sequence coding for the protein, or a functional equivalent as described in Section 4.1 supra, was inserted into an appropriate expression vector, i.e., a vector which contains the necessary elements for the transcription and translation of the inserted coding sequence.

More specifically, methods which are well known to those skilled in the art can be used to construct expression vectors containing the C-proteinase sequence and appropriate transcriptional/translational control signals. These methods include in vitro recombinant DNA techniques, synthetic techniques and in vivo recombination/genetic recombination. See e.g., the techniques described in Maniatis et al., 1989, *Molecular Cloning A Laboratory Manual,* Cold Spring Harbor Laboratory, N.Y. and Ausubel et al., 1989,

*Current Protocols in Molecular Biology,* Greene Publishing Associates and Wiley Interscience, N.Y.

A variety of host-expression vector systems may be utilized to express the C-proteinase coding sequence. These include but are not limited to microorganisms such as bacteria transformed with recombinant bacteriophage DNA, plasmid DNA or cosmid DNA expression vectors containing the C-proteinase coding sequence; yeast transformed with recombinant yeast expression vectors containing the C-proteinase coding sequence; insect cell systems infected with recombinant virus expression vectors (e.g., bacculovirus) containing the C-proteinase coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the C-proteinase coding sequence; or animal cell systems infected with recombinant virus expression vectors (e.g., adenovirus, vaccinia virus, human tumor cells (including HT-1080)) including cell lines engineered to contain multiple copies of the C-proteinase DNA either stably amplified (CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage X, plac, ptrp, ptac (ptrp-lac hybrid promoter) and the like may be used; when cloning in insect cell systems, promoters such as the bacculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the C-proteinase DNA SV40-, BPV- and EBV-based vectors may be used with an appropriate selectable marker.

In bacterial systems, a number of expression vectors may be advantageously selected depending upon the use intended for the C-proteinase expressed. For example, when large quantities of C-proteinase are to be produced to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the C-proteinase coding sequence may be ligated into the vector in frame with the lac Z coding region so that a hybrid AS-lac Z protein is produced; pIN vectors (Inouye & Inouye, 1985, *Nucleic Acids Res.* 13:3101–3109; Van Heeke & Schuster, 1989, *J. Biol. Chem.* 264:5503–5509); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned polypeptide of interest can be released from the GST moiety.

In yeast, a number of vectors containing constitutive or inducible promoters may be used. For a review see, *Current Protocols in Molecular Biology,* Vol. 2, 1988, Ed. Ausubel et al., Greene Publish. Assoc. & Wiley Interscience, Ch. 13; Grant et al., 1987, *Expression and Secretion Vectors for Yeast,* in Methods in Enzymology, Eds. Wu & Grossman, 1987, Acad. Press, N.Y., Vol. 153, pp. 516–544; Glover, 1986, *DNA Cloning,* Vol. II, IRL Press, Wash., D.C., Ch. 3; Bitter, 1987, *Heterologous Gene Expression in Yeast,* Methods in Enzymology, Eds. Berger & Kimmel, Acad. Press, N.Y., Vol. 152, pp. 673–684; and *The Molecular Biology of the Yeast Saccharomyces,* 1982, Eds. Strathern et al., Cold Spring Harbor Press, Vols. I and II.

In cases where plant expression vectors are used, the expression of the C-proteinase coding sequence may be driven by any of a number of promoters. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J.* 6:307–311) may be used; alternatively, plant promoters such as the small subunit of RUBISCO (Coruzzi et al., 1984, *EMBO J.* 3:1671–1680; Broglie et al., 1984, *Science* 224:838–843); or heat shock promoters, e.g., soybean hsp17.5-E or hsp17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, *Methods for Plant Molecular Biology,* Academic Press, N.Y., Section VIII, pp. 421–463; and Grierson & Corey, 1988, *Plant Molecular Biology,* 2d Ed., Blackie, London, Ch. 7–9.

An alternative expression system which could be used to express C-proteinase is an insect system. In one such system, Bacculovirus is used as a vector to express foreign genes. The virus then grows in the insect cells. The C-proteinase coding sequence may be cloned into non-essential regions (for example the polyhedrin gene) of the virus and placed under control of a Bacculovirus promoter. These recombinant viruses are then used to infect insect cells in which the inserted gene is expressed. (E.g., see Smith et al., 1983, *J. Viol.* 46:584; Smith, U.S. Pat. No. 4,215,051).

In mammalian host cells, a number of viral based expression systems may be utilized. In cases where an adenovirus is used as an expression vector, the C-proteinase coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing C-proteinase in infected hosts. See e.g., Logan & Shenk, 1984, *Proc. Natl. Acad. Sci.* (USA) 81:3655–3659. Alternatively, the vaccinia 7.5K promoter may be used. See, e.g., Mackett et al., 1982, *Proc. Natl. Acad. Sci.* (USA) 79:7415–7419; Mackett et al., 1984, *J. Virol.* 49:857–864; Panicali et al., 1982, *Proc. Natl. Acad. Sci.* 79:4927–4931.

In a preferred embodiment, the C-proteinase sequence is expressed in human tumor cells, and more preferably HT-1080, which have been stably transfected with calcium phosphate precipitation and a neomycin resistance gene.

Specific initiation signals may also be required for efficient translation of inserted C-proteinase coding sequences.

These signals include the ATG initiation codon and adjacent sequences. In cases where the entire C-proteinase gene, including its own initiation codon and adjacent sequences, is inserted into the appropriate expression vector, no additional translational control signals may be needed. However, in cases where only a portion of the C-proteinase coding sequence is inserted, exogenous translational control signals, including the ATG initiation codon, must be provided. Furthermore, the initiation codon must be in phase with the reading frame of the C-proteinase coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. See e.g., Bitter et al., 1987, *Methods in Enzymol.* 153:516–544.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, HT-1080 etc.

For long-term, high-yield production of recombinant proteins, stable expression is preferred. For example, cell lines which stably express C-proteinase may be engineered. Rather than using expression vectors which contain viral origins of replication, host cells can be transformed with C-proteinase DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowy, et al., 1980, *Cell* 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, *Proc. Natl. Acad. Sci. USA* 77:3567; O'Hare, et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA* 85:8047), and ODC (ornithine decarboxylase) which confers resistance to the ornithine decarboxylase inhibitor, 2-(difluoromethyl)-DL-ornithine, DFMO (McConlogue, 1987, In: *Current Communications in Molecular Biology*, Cold Spring Harbor Laboratory ed.).

D. Identification of Transfectants or Transformants that Express C-Proteinase The host cells which contain the coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of C-proteinase mRNA transcripts in the host cell; and (d) detection of the gene product as measured by an assay or by its biological activity.

In the first approach, the presence of the C-proteinase coding sequence inserted in the expression vector can be detected by DNA-DNA or DNA-RNA hybridization using probes comprising nucleotide sequences that are homologous to the C-proteinase coding sequence, respectively, or portions or derivatives thereof.

In the second approach, the recombinant expression vector/host system can be identified and selected based upon the presence or absence of certain "marker" gene functions (e.g., resistance to antibiotics, resistance to methotrexate, transformation phenotype, occlusion body formation in bacculovirus, etc.). For example, in a preferred embodiment, the C-proteinase coding sequence is inserted within a neomycin-resistance marker gene sequence of the vector, and recombinants containing the C-proteinase coding sequence can be identified by the absence of the marker gene function. Alternatively, a marker gene can be placed in tandem with the C-proteinase sequence under the control of the same or different promoter used to control the expression of the C-proteinase coding sequence. Expression of the marker in response to induction or selection indicates expression of the C-proteinase coding sequence.

In the third approach, transcriptional activity for the C-proteinase coding region can be assessed by hybridization assays. For example, RNA can be isolated and analyzed by Northern blot using a probe homologous to the C-proteinase coding sequence or particular portions thereof. Alternatively, total nucleic acids of the host cell may be extracted and assayed for hybridization to such probes.

The fourth approach involves the detection of the biologically active C-proteinase gene product. A number of assays can be used to detect C-proteinase activity including but not limited to those assays described in Kessler and Goldberg, 1978, *Anal. Biochem.* 86:463 and Njieha et al., 1982, *Biochemistry* 21:757–764.

E. Screening of Peptide Library with C-Proteinase or Engineered Cell Lines

Random peptide libraries consisting of all possible combinations of amino acids attached to a solid phase support may be used to identify peptides that are able to modulate and/or inhibit C-proteinase activity by binding to C-proteinase. The screening of peptide libraries may have therapeutic value in the discovery of pharmaceutical agents that act to inhibit the biological activity of the protein.

Identification of molecules that are able to bind to C-proteinase may be accomplished by screening a peptide library with recombinant soluble C-proteinase. Methods for expression and purification of the enzyme are described above and may be used to express recombinant full length C-proteinase or fragments, analogs, or derivatives thereof depending on the functional domains of interest.

To identify and isolate the peptide/solid phase support that interacts and forms a complex with C-proteinase it is necessary to label or "tag" the C-proteinase molecule. The C-proteinase protein may be labelled according to well-known techniques, including iodination labelling with $^{125}$I. Additionally, the C-proteinase protein also may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label, to C-proteinase, may be performed using techniques that are routine in the art. Alternatively, C-proteinase expression vectors may be engineered to express a chimeric protein containing an epitope for which a commercially available antibody exist. The epitope specific antibody may be tagged using methods well known in the art including labeling with enzymes, fluorescent dyes or colored or magnetic beads.

The "tagged" C-proteinase is incubated with the random peptide library for 30 minutes to one hour at 22° C. to allow complex formation between C-proteinase and peptide species within the library. The library is then washed to remove any unbound protein. If C-proteinase has been conjugated to alkaline phosphatase or horseradish peroxidase the whole library is poured into a petri dish containing a substrates for either alkaline phosphatase or peroxidase, for example, 5-bromo-4-chloro-3-indoyl phosphate (BCIP) or 3,3',4,4"-diamnobenzidine (DAB), respectively. After incubating for several minutes, the peptide/solid phase-C-proteinase complex changes color, and can be easily identified and isolated physically under a dissecting microscope with a micromanipulator. If a fluorescent tagged C-proteinase molecule has been used, complexes may be isolated by fluorescent activated sorting. If a chimeric C-proteinase expressing a heterologous epitope has been used, detection of the peptide/C-proteinase complex may be accomplished by using a labeled epitope specific antibody. Once isolated, the identity of the peptide attached to the solid phase support may be determined by peptide sequencing.

F. Screening of Organic Compounds with C-Proteinase Protein or Engineered Cell Lines Cell lines that express C-proteinase may be used to screen for molecules that modulate C-proteinase activity or collagen formation. Such molecules may include small organic or inorganic compounds, or other molecules that modulate C-proteinase activity or that promote or prevent the formation of collagen. Synthetic compounds, natural products, and other sources of potentially biologically active materials can be screened in a number of ways.

The ability of a test molecule to interfere with C-proteinase-procollagen binding and/or C-proteinase-processing enzyme binding may be measured using standard biochemical techniques. Other responses such as activation or suppression of catalytic activity may also be monitored. These assays may be performed using conventional techniques developed for these purposes in the course of screening.

G. Generation Peptide Substrates of C-Proteinase

Peptides corresponding to the C-proteinase cleavage site of procollagen may be synthesized. Such peptides would be expected to have affinity to the active site of C-proteinase enzyme, and they may be cleaved by C-proteinase as the C-propeptides of naturally occurring procollagen. Peptides resembling the cleavage site of procollagen therefore may be useful (1) as inhibitors of C-proteinase activity for therapeutical applications, or (2) as convenient C-proteinase substrates for the screening for compounds which interfere with the enzymatic activity of C-proteinase.

In one aspect, peptides resembling the C-proteinase binding site of procollagen can be used to modulate the physiological activity of C-proteinase, by, for example, acting as a competitive inhibitor. Specifically, such peptides, having affinity to the active site of C-proteinase, may compete with the natural substrate, i.e., procollagen, for binding sites of the enzyme. Accordingly, an excess of such peptides will competitively inhibit cleavage of the C-propeptides from procollagen, thereby preventing or regulating an essential step in the generation of mature collagen. See, Section 2, supra. Thus, these peptides have broad application as therapeutical means for the treatment of diseases related to unregulated production of collagen.

Preferably, the affinity of the peptides to C-proteinase is similar to or higher than that of the natural C-proteinase substrate, i.e., procollagen. For use as competitive inhibitors, the peptides may be cleaved upon binding to the active site of C-proteinase, or, alternately, may stay attached to the active site of the enzyme, without ever being cleaved.

The ability of a peptide to bind to C-proteinase and to interfere with C-proteinase's binding to procollagen may be measured using standard biochemical techniques. See, supra. Where the peptide is cleaved by C-proteinase, cleavage may be measured by reduction of the peptide size using standard means.

In another aspect of the invention , peptides mimicking the C-proteinase cleavage sites are used to screen arrays of molecules to identify compounds capable of modifying C-proteinase enzymatic activity. Screening of peptide libraries or other libraries comprising chemical compounds is essentially performed as described, supra. Preferably, the peptide used to identify compounds, peptides or molecules which modify C-proteinase activity is cleaved by C-proteinase.

In another specific embodiment, a peptide being cleaved by active C-proteinase is attached to a fluorogenic identifier tag. Cleavage, i.e., physical separation of a peptide into two halves results in a dramatic increase of fluorescence of this particular peptide. Yaron et al., 1979, *Analytical Biochemistry* 95:228–235. Such fluorogenic peptide will be a convenient and powerful means to be used for high throughput screening to identify inhibitors of C-proteinase as well as for measuring C-proteinase activity and its inhibition for any other experimental purpose.

Various embodiments are described below for screening, identification and evaluation of compounds that interact with C-proteinase or its targets, which compounds may affect various cellular processes including the formation and production of collagen.

The following preparations and examples are given to enable those skilled in the art to more clearly understand and to practice the present invention. The present invention is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Generation of Peptide Substrates as C-Proteinase Inhibitors

A variety of short peptides comprising five (5) to twelve (12) amino acids was synthesized and tested for cleavage by active C-proteinase.

First, four peptides, each comprising eight (8) amino acids corresponding to the cleavage region of several procollagens were synthesized. See, TABLE 1, SEQ ID NO:3, SEQ ID NO:4, SEQ ID NO:5, and SEQ ID NO:6. All four peptides were examined for cleavability by C-proteinase. As indicated in TABLE 1, all four peptides were cleaved by C-proteinase, which seemed to be a lucky but yet unexpected result. Indeed, one would expect that recognition of the cleavage site depends on structural requirements which cannot be resembled by only eight (8) amino acids. One of these peptides, however, i.e., the peptide comprising SEQ ID NO:6, was cleaved much more efficiently than the three others.

Second, a series of peptides was prepared based on the sequence of original peptide SEQ ID NO:6. Specifically, peptides were designed resembling the core of the peptide comprising SEQ ID NO:6, but with truncations of one, two and three amino acids from either side of the cleavage site. A further peptide was synthesized resembling two additional amino acids at both the N-terminus and C-terminus of the original peptide comprising SEQ ID NO:6.

The relative cleavage activity of C-proteinase against these peptides was evaluated and is shown in TABLE 1. Significantly, expanding the length of the peptide did not impact its cleavability by C-proteinase (SEQ ID NO:7). Also, removing one amino acid from either end of the peptide did not drastically alter its cleavability (SEQ ID NO:8 and SEQ ID NO:11). Removing two or more amino acids from either end of the original SEQ ID NO:6 sequence, however, yielded a non-cleavable peptide (SEQ ID NOS:9, 10, 12, 13).

TABLE 1

Cleavability Of Peptides Resembling The C-Proteinase Cleavage Site Of Procollagen

| SEQ ID NO | Sequence[1] | Corresponding Collagen | Cleavability |
|---|---|---|---|
| | cleavage site ↓ | | |
| 3 | Ac-YYRA-DDAN-NH$_2$ | α1(I) | slight |
| 4 | Ac-FYRA-DQPR-NH$_2$ | α2(I) | slight |
| 5 | Ac-YMRA-DQAA-NH$_2$ | α1(II) | slight |
| 6 | Ac-PYYG-DEPM-NH$_2$ | α1(III) | excellent |
| 7 | Ac-FAPYYG-DEPMDF-NH$_2$ | α1(III) | excellent |
| 8 | Ac-PYYG-DEP-NH$_2$ | α1(III) | excellent |
| 9 | Ac-PYYG-DE-NH$_2$ | α1(III) | none |
| 10 | Ac-PYYG-D-NH$_2$ | α1(III) | none |
| 11 | Ac-YYG-DEPM-NH$_2$ | α1(III) | excellent |
| 12 | Ac-YG-DEPM-NH$_2$ | α1(III) | none |
| 13 | Ac-G-DEPM-NH$_2$ | α1(III) | none |

[1]Amino Acid Code: A alanine; D asparatic acid; E glutamic acid; F phenylalanine; G glycine; M methionine; P proline; Y tyrosine; R arginine; Ac = acetyl; NH$_2$ = amide.

The peptides shown in TABLE 1 and identified as SEQ ID NOS: 3, 4, 5, 6, 7, 8, 9, 10, 11, 12, and 13 are acetylated at the amino-terminus and amidated at the carboxy-terminus. They are functionally equivalent to the unmodified peptides identified as SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24.

All references cited within the body of the instant specification are hereby incorporated by reference in their entirety.

What is claimed is:

1. A peptide which is cleaved by a polypeptide selected from the group consisting of SEQ ID NO:1 and SEQ ID NO:2, wherein said peptide
    (a) corresponds to a fragment of a naturally occurring procollagen which comprises a cleavage sequence for C-proteinase, said cleavage sequence selected from the group consisting of Ala-Asp-Glu and Gly-Asp-Glu, and
    (b) contains from 7 to 12 amino acid residues.

2. A peptide which is cleaved by a polypeptide selected from the group consisting of SEQ ID NO:1 and SEQ ID NO:2, wherein said peptide
    (a) corresponds to a fragment of a naturally occurring procollagen which comprises a cleavage sequence for C-proteinase, said cleavage sequence being Ala-Asp-Asp, and
    (b) contains from 8 to 12 amino acid residues.

3. A peptide having a sequence selected from the group consisting of SEQ ID NO:6 and SEQ ID NO:17.

4. A peptide having a sequence selected from the group consisting of SEQ ID NO:7 and SEQ ID NO:18.

5. A peptide having a sequence selected from the group consisting of SEQ ID NO:8 and SEQ ID NO:19.

6. A peptide having a sequence selected from the group consisting of SEQ ID NO:11 and SEQ ID NO:22.

7. A peptide having a sequence selected from the group consisting of SEQ ID NO: 3, SEQ ID NO:4, SEQ ID NO:5, SEQ ID NO:14, SEQ ID NO:15 and SEQ ID NO:16.

8. A peptide which is cleaved by a polypeptide selected from the group consisting of SEQ ID NO:1 and SEQ ID NO:2, wherein said peptide
    (a) is a fragment of human type III procollagen comprising the amino acid sequence Gly-Asp-Glu, and
    (b) contains from 7 to 12 amino acid residues.

9. A peptide which is cleaved by a polypeptide selected from the group consisting of SEQ ID NO:1 and SEQ ID NO:2, wherein said peptide
    (a) is a fragment of human type I procollagen comprising the amino acid sequence Ala-Asp-Asp, and
    (b) contains from 8 to 12 amino acid residues.

10. A peptide which is cleaved by a polypeptide selected from the group consisting of SEQ ID NO:1 and SEQ ID NO:2, wherein said peptide
    (a) is a fragment of human type I procollagen comprising the amino acid sequence Ala-Asp-Glu, and
    (b) contains from 7 to 12 amino acid residues.

11. A peptide which is cleaved by a polypeptide selected from the group consisting of SEQ ID NO:1 and SEQ ID NO:2, wherein said peptide (a) is a fragment of human type II procollagen comprising the amino acid sequence Ala-Asp-Glu, and (b) contains from 7 to 12 amino acid residues.

12. A peptide having a sequence selected from the group consisting of SEQ ID NO:6, SEQ ID NO:7, SEQ ID NO:8, SEQ ID NO:11, SEQ ID NO:17, SEQ ID NO:18 SEQ ID NO:19 and SEQ ID NO:22.

13. The peptide of claim 1, 8, 9, 10, 11, or 2, said peptide being attached to a fluorophore.

14. The peptide of claim 3, 4, 5, 6, or 7, said peptide being attached to a fluorophore.

* * * * *